United States Patent [19]

Phares

[11] Patent Number: 5,693,498
[45] Date of Patent: Dec. 2, 1997

[54] DNA ENCODING A PLEROCERCIOD GROWTH FACTOR

[75] Inventor: Cleveland Kirk Phares, Omaha, Nebr.

[73] Assignee: The Board of Regents of The University of Nebraska, Lincoln, Nebr.

[21] Appl. No.: 546,712

[22] Filed: Oct. 23, 1995

Related U.S. Application Data

[63] Continuation-in-part of Ser. No. 803,682, Dec. 3, 1991, abandoned, which is a continuation of Ser. No. 465,586, Jan. 17, 1990, abandoned, which is a continuation of Ser. No. 355,882, May 19, 1989, abandoned, which is a continuation of Ser. No. 887,222, Jun. 20, 1986, abandoned.

[51] Int. Cl.$^6$ .................. C12N 15/18; C12N 1/21; C12N 5/10; C12N 15/63
[52] U.S. Cl. .............. 435/69.4; 435/243; 435/320.1; 435/325; 536/23.51
[58] Field of Search .................. 530/399; 435/69.4, 435/70.1, 252.3, 320.1, 243, 325; 536/23.1, 23.51

[56] References Cited

U.S. PATENT DOCUMENTS 3,853,833  12/1974  Li ........................................... 260/112.5

OTHER PUBLICATIONS

Abstract No. 57632p, Phares, C.K., "Isolation by Polyacrylamide Gel Electrophoresis of the Growth Factor From Plerocercoids of the Tapeworm, Spirometra Masonoides", Chemical Abstracts, vol. 80, 1974; *Prep. Biochem*, 1973 3(4), 375–81.

Abstract No. 98:174998v, Friedman, "Characterization of Cobalamin Receptor Sites in Brush–Border Plasma Membranes of the Tapeworm Spirometra Masonoides", Chemical Abstracts, vol. 98, 1983; *J. Biol. Chem*, 1983,258(7), 4261–5.

Abstract No. 97:124372v, Friedman, "Spirometra Mansonoides: Lectin Analysis of Tegumental Glycopeptides", Chemical Abstracts, vol 97, 1982; *Exp. Parasitol*, 1982, 54(1), 93–103.

Phares, "A Method for Solubilization of a Human Growth Hormone Analogue From Plerocercoids of Spirometra Mansonoides", *The Journal of Parasitology*, vol. 70, No. 5, Oct. 1984, pp.840–842.

Primary Examiner—John Ulm
Assistant Examiner—Christine Saoud
Attorney, Agent, or Firm—Zarley, McKee, Thomte, Voorhees & Sease

[57] ABSTRACT

A DNA sequence encoding plerocercoid growth factor is disclosed. The plerocercoid growth factor is an active growth factor in human beings and is not diabetogenic.

4 Claims, 7 Drawing Sheets

```
CTT CCC GAC AGT GTT AAT TGG CAC GAG AAG GGT GCT GTT ACA TCG GTC        48
Leu Pro Asp Ser Val Asn Trp His Glu Lys Gly Ala Val Thr Ser Val
 1                   5                  10                  15

AAA AAT CAG GGT CAG TGC GGA TCC TGT TGG TCT TTC TCC GCA AAC GGT        96
Lys Asn Gln Gly Gln Cys Gly Ser Cys Trp Ser Phe Ser Ala Asn Gly
                20                  25                  30

GCC ATT GAG GGC GCA ATT CAG ATA AAG ATG GGG ATA CTG CGC AGC CTC       144
Ala Ile Glu Gly Ala Ile Gln Ile Lys Met Gly Ile Leu Arg Ser Leu
                35                  40                  45

TCA GAA CAA CAG TTG GTT GAC TGC AGT TGG GAG TAT GGA AAC CAA GGC       192
Ser Glu Gln Gln Leu Val Asp Cys Ser Trp Glu Tyr Gly Asn Gln Gly
                50                  55                  60

TGC AAT GGA GGG TTT ATG TCG CTG GCT TTT CAA TAC GCT CAA AGG TAC       240
Cys Asn Gly Gly Phe Met Ser Leu Ala Phe Gln Tyr Ala Gln Arg Tyr
65                  70                  75                  80

GGC GTA GAA GCT GAA GTT GAC TAC AGA TAT ACT GCA AAG GAC GGG TTT       288
Gly Val Glu Ala Glu Val Asp Tyr Arg Tyr Thr Ala Lys Asp Gly Phe
                85                  90                  95
```

Fig. 1A

| | | | | | | |
|---|---|---|---|---|---|---|
| TGT | AGA | TAT | CAA | CAG | GAC | ATG | GTT | GCC | AAT | GTT | ACT | GGA | TAT | GCA |
| Cys | Arg | Tyr | Gln | Gln | Asp | Met | Val | Ala | Asn | Val | Thr | Gly | Tyr | Ala |
|     |     |     | 100 |     |     |     | 105 |     |     |     |     | 110 |     |     | 336 |

| GAG | CTA | CCA | CAG | GGC | GAT | GAA | GCA | AGC | CTC | CAG | AGA | GCT | GCA | GTC |
| Glu | Leu | Pro | Gln | Gly | Asp | Glu | Ala | Ser | Leu | Gln | Arg | Ala | Val | Val |
|     |     | 115 |     |     |     |     | 120 |     |     |     |     | 125 |     |     | 384 |

| ATA | GGG | CCC | ATA | TCT | GTT | GGA | ATC | GAT | GCA | AAC | GAT | CCC | GGA | TTT | ATG |
| Ile | Gly | Pro | Ile | Ser | Val | Gly | Ile | Asp | Ala | Asn | Asp | Pro | Gly | Phe | Met |
|     | 130 |     |     |     |     | 135 |     |     |     |     | 140 |     |     |     |     | 432 |

| TCT | TAC | AGC | CAC | GGT | GTG | TTT | GTT | AGC | AAA | ACA | TGC | TCC | CCA | GAT | GAC |
| Ser | Tyr | Ser | His | Gly | Val | Phe | Val | Ser | Lys | Thr | Cys | Ser | Pro | Asp | Asp |
|     | 145 |     |     |     |     | 150 |     |     |     |     | 155 |     |     |     | 160 | 480 |

| ATT | AAT | CAC | GGC | GTT | CTG | GTC | ATC | GGT | TAT | GGC | ACG | GAA | AAT | GAC | GAG |
| Ile | Asn | His | Gly | Val | Leu | Val | Ile | Gly | Tyr | Gly | Thr | Glu | Asn | Asp | Glu |
|     |     | 165 |     |     |     |     | 170 |     |     |     |     | 175 |     |     |     | 528 |

| CCT | TAC | TGG | CTG | GTA | AAG | AAC | AGC | TGG | GGG | CGC | TCC | TGG | GAA | CAG |
| Pro | Tyr | Trp | Leu | Val | Lys | Asn | Ser | Trp | Gly | Arg | Ser | Trp | Gly | Gln |
|     |     |     | 180 |     |     |     |     | 185 |     |     |     |     | 190 |     | 576 |

*Fig. 1B*

```
GGA TAC GTC AAA ATG GCC CGC AAC AAC ATG TGT GGA ATT GCC    624
Gly Tyr Val Lys Met Ala Arg Asn Asn Met Cys Gly Ile Ala
        195                 200                 205

AGC GTG GCA TCT TAT CCA ACC GTG TAA                         651
Ser Val Ala Ser Tyr Pro Thr Val
        210
```

Fig. 1C

```
Leu Pro Asp Ser Val Asn Trp His Glu Lys Gly Ala Val Thr Ser Val
  1               5                  10                  15
Lys Asn Gln Gly Gln Cys Gly Ser Cys Trp Ser Phe Ser Ala Asn Gly
                 20                  25                  30
Ala Ile Glu Gly Ala Ile Gln Ile Lys Met Gly Ile Leu Arg Ser Leu
                 35                  40                  45
Ser Glu Gln Leu Val Asp Cys Ser Trp Glu Tyr Gly Asn Gln Gly
                 50                  55                  60
Cys Asn Gly Gly Phe Met Ser Leu Ala Phe Gln Tyr Ala Gln Arg Tyr
 65                  70                  75                  80
Gly Val Glu Ala Glu Val Asp Tyr Arg Tyr Thr Ala Lys Asp Gly Phe
                 85                  90                  95
Cys Arg Tyr Gln Gln Asp Met Val Val Ala Asn Val Thr Gly Tyr Ala
                100                 105                 110
Glu Leu Pro Gln Gly Asp Glu Ala Ser Leu Gln Arg Ala Val Ala Val
                115                 120                 125
```

Fig. 2A

Ile Gly Pro Ile Ser Val Gly Ile Asp Ala Asn Asp Pro Gly Phe Met
130                         135                     140                         160

Ser Tyr Ser His Gly Val Phe Val Ser Lys Thr Cys Ser Pro Asp Asp
145                         150                     155                         160

Ile Asn His Gly Val Leu Val Ile Gly Tyr Gly Thr Glu Asn Asp Glu
                            165                     170                         175

Pro Tyr Trp Leu Val Lys Asn Ser Trp Gly Arg Ser Trp Gly Glu Gln
                            180                     185                         190

Gly Tyr Val Lys Met Ala Arg Asn Lys Asn Asn Met Cys Gly Ile Ala
                            195                     200                         205

Ser Val Ala Ser Tyr Pro Thr Val
210                         215

Fig. 2B

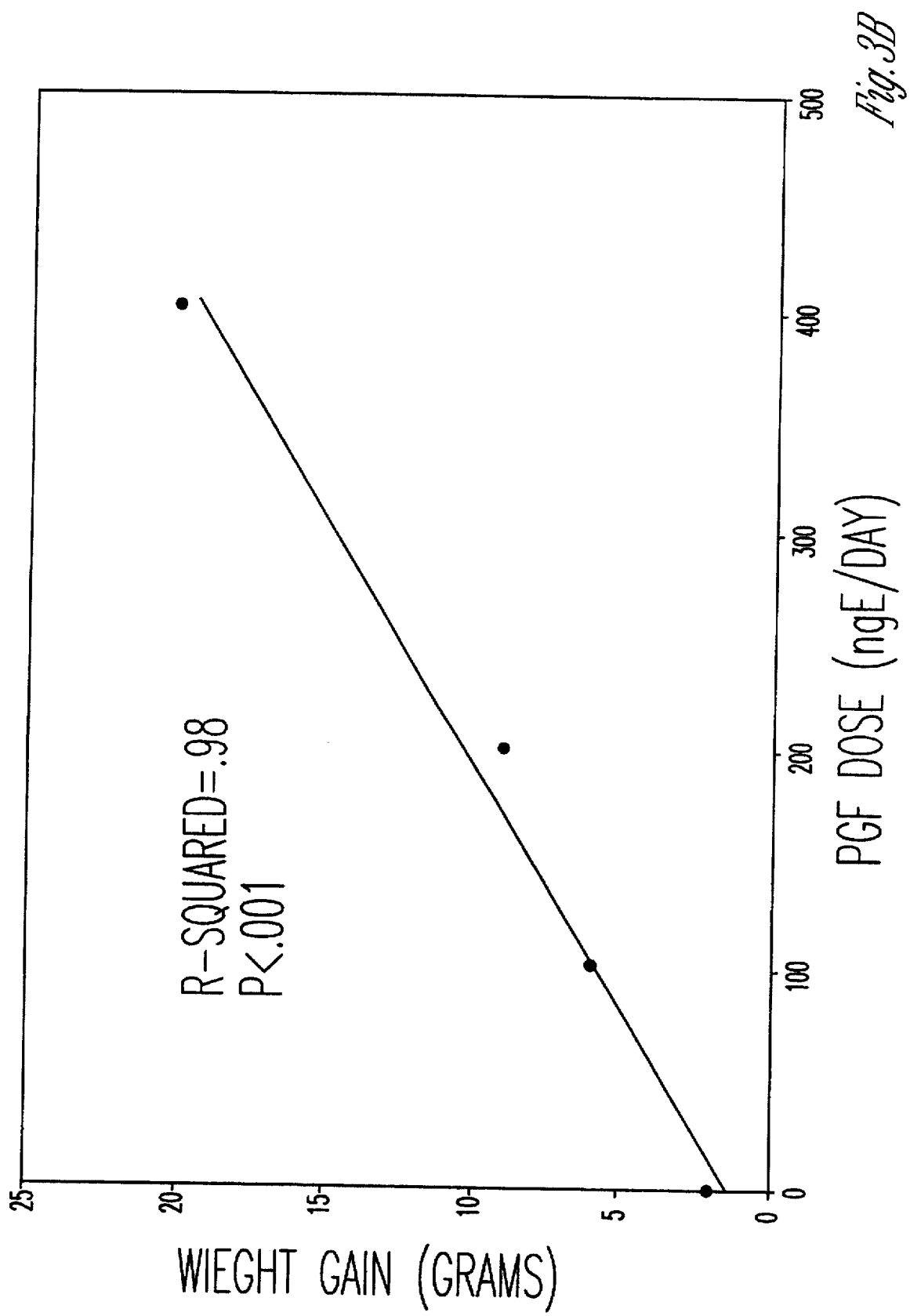

1

DNA ENCODING A PLEROCERCIOD GROWTH FACTOR

CROSS-REFERENCE TO A RELATED APPLICATION

This application is a continuation-in-part application of prior U.S. patent application Ser. No. 07/803,682 filed by Cleveland Kirk Phares on Dec. 3, 1991, now abandoned, which is a continuation of U.S. patent application Ser. No. 07/465,586 filed Jan. 17, 1990 now abandoned, which is a continuation of U.S. patent application Ser. No. 07/355,882 filed May 19, 1989 now abandoned, which is a continuation of U.S. patent application Ser. No. 06/887,222 filed Jun. 20, 1986 now abandoned. All of said applications are commonly owned.

BACKGROUND OF THE INVENTION

This invention relates to growth hormones and more particularly to drugs which promote growth other than the human pituitary growth hormone.

Hormones are known which stimulate growth in animals by exerting a direct effect on protein, carbohydrate and lipid metabolism and control the rate of skeletal and visceral growth. Such hormones may act on more than one species although this is not necessarily true of all such hormones. Hormones are normally obtained from the animals which produce them and may be used in different therapies to stimulate growth.

One type of hormone, a human growth hormone (HGH), sometimes referred to as a pituitary hormone, is a straight chain of 191 amino acids without carbohydrate substituents. It has a molecular weight of 21,500 daltons determined by the DISC (discontinuous) gel electrophoresis method and has an isoelectric point of 4.9. The amino acid sequence for HGH is disclosed in U.S. Pat. No. 3,853,833 to Choh Li and is incorporated herein by reference.

This hormone is obtained from the human pituitary gland by elution chromatography and has been used therapeutically to stimulate growth in children deficient in growth hormone in doses usually less than 8 milligrams per day for periods sometimes exceeding 10 years. Doses of human growth hormone of 8 milligrams per day have been known to: (1) cause impairment of glucose tolerance in humans; and (2) stimulate glucose incorporation into adopose tissue, lipids and liver provided they do not have the hormone present in them.

This human pituitary hormone has several disadvantages such as: (1) it produces resistance to insulin; (2) it is diabetogenic; (3) it increases blood glucose; (4) it stimulates the breakdown of body fat; (5) it stimulates an increase in tissue receptors for the hormones prolactin and estrogen; and (6) it induces diabetes if given in large doses for extended periods of time as indicated by reduced glucose tolerance, such periods of time and dosages are sufficiently low so as preclude the use of this hormone for certain types of therapy.

It is known from the publication of Mueller, J. F. in 1963 entitled "Parasite-Induced Weight Gain in Mice" *J. Parasitol*, 113:217, that infection by the plerocercoid stage of the tapeworm, *Spirometra mansonoides*, stimulates body growth and it is known from the publications of Garland, J. T. et al, in 1971 entitled "Induction of Sulfation Factor Activity by Infection of Hypophysectomized Rats with *Spirometra mansonoides*" *Indocrinology*, 88:924 and the publication by Steelman et al, in 1970 entitled "Growth Hormone-Like Activity in Hypophysectomized Rats Implanted with *Spirometra mansonoides* spargana" *Proc. of the Soc. of Exp. Biol. Med.*, 133:269, that plerocercoid injected into rats suppresses endogenous growth hormone levels and elicits other responses indicative of functional similarities to growth hormones.

The prior art describes processes for obtaining an impure drug from the plerocercoids of tapeworms and has shown that this drug competitively inhibits human growth hormone binding to its receptors in hepatic miscrosomes from female rabbits and cross reacts with anti-human growth hormone monoclonal antibodies. For example, the publication of Phares, C. K. in 1984 entitled "A Method for Solubilization of Human Growth Hormone Analog from Plerocercoids of *Spirometra mansonoides*", *J. Parasitol*, 70:840, described obtaining this drug in impure form and showing it to be an active growth factor. The drug was obtained by solubilization of the plerocercoid membranes with a non-ionic detergent. However, the purified growth factor only had a specific activity of 50 to 80 ngE (nanograms equivalent of a human growth hormone standard)/mg of protein (nanograms of the eluant for each milligram of protein). Quite surprisingly, however, applicant has characterized the amino acid sequence of plerocercoid growth factor and it has no homology to human growth hormone or any other growth hormone despite these early indications that there would be a high level of homology.

It has been known to remove human growth hormone by receptor affinity chromatography using liver membranes prepared from late pregnant rabbits. However, it was not known that affinity chromatography would be useful in purifying the growth factor in the plerocercoid stage of *Spirometra mansonoides*, and given the lack of homology between the two proteins it would not be expected that pleroceroid growth factor could be purified by this method.

It is an object of the invention to provide a novel drug for the treatment of growth related disorders.

It is a further object of the invention to provide a novel method for making a drug which stimulates growth in animals.

It is a still further object of the invention to provide novel methods of treatment for growth-affected diseases.

It is a still further object of the invention to provide a novel drug and method of using it to treat isolated growth hormone deficiency (hyposomatotrophic dwarfism).

It is a still further object of the invention to provide a novel drug and method of using the drug to treat normal variant short stature.

It is a still further object of the invention to provide a novel drug and method of using the drug to treat massive and uncontrolled bleeding of stress ulcers.

It is a still further object of the invention to provide a novel protein for promoting growth which does not have diebetogenicity.

It is a still further object of the invention to provide a novel protein for promoting growth which substance may be administered in higher doses and for longer periods of time than human growth hormone.

It is a still further object of the invention to provide a novel drug and method of using the drug for gastrointestinal tract diseases.

It is a still further object of the invention to provide a novel drug and method of using the drug to stimulate body growth in animals while reducing the amount of the animal's own growth hormone developed in the animal.

It is a still further object of the invention to provide a novel drug and method of using the drug to treat anorexia nervosa.

It is a still further object of the invention to a drug and method of using the drug for the treatment of anorexia nervosa without complications of diabetes mellitus, or hormone related cancers such as mammary cancer.

It is a still further object of the invention to provide a novel drug and method of using the drug to increase the growth rate and feed conversion of livestock.

It is a still further object of the invention to provide a novel substance which is substantially identical to human growth hormone in its receptor binding and activation properties but contains certain minor differences which make it a superior drug.

It is a still further object of this invention to provide a novel drug for the prevention and treatment of mammary cancer.

SUMMARY OF THE INVENTION

In accordance with the above and further objects of the invention, an amino acid chain, a single chain, forming a single compound without carbohydrate substituents has a molecular weight of 23,618 and an isoelectric point of 4.5 and a polypeptide consisting of 216 amino acids has been purified and isolated from Spirometra mansonoides, the underlying cDNA sequence encoding this protein has also been characterized.

An antibody to human growth hormone reacts with it and it is capable of stimulating growth in humans and other animals in a manner similar to the human growth hormone.

It: (1) is highly hydrophobic; (2) has insulin-like effects; and 3) stimulates glucose incorporation into both lipids and adopose tissue as well as in the liver. It competitively inhibits HGH binding to receptors in the liver. It also has an amino acid sequence and cDNA sequence which exhibit no homology to any other growth hormone or even to any other growth hormone.

This substance is obtained by separating it from the plerocercoid stage of Spirometra mansonoides and purifying it. Preferably, it is solubilized before purification. Generally, the plerocercoids are homogenized and the substance which promotes growth is removed. The substance is dissolved in the presence of a dispersing agent which is preferably non-ionic.

More specifically, plerocercoid is homogenized in a mixture of Triton X-100 (1.0 percent). Triton is a trademark of Rohm and Hass Co., Independence Mall West, Philadelphia, Pa. 19105, and has as its principal ingredient 4-(1,1,3,3-tetramethylbutyl) phenol polymer with formaldehyde and oxirane. It is a non-ionic detergent with surface-tension-reducing properties. After preliminary separation, receptor affinity chromatography using rabbit liver receptor sites for HGH is used.

The purified protein has been characterized and sequenced and quite unexpectedly the novel sequence showed no homology to human growth hormone. The cDNA sequence has also been characterized making possible the large scale production of the protein without having to isolate it from the tapeworm.

For therapeutic purposes, the substance having the characteristic of stimulating growth is introduced into the subject with doses equivalent to at least 10 international units of GH per day for at least two days and may be between 10 and 20 international units per day for an extended period of time. The dosage depends on the disease being treated and is normally injected into the blood stream.

Some of the diseases for which it may be used are hyposomatotrophic dwarfism, normal variant short stature, massive and uncontrolled bleeding of stress ulcers, anorexia nervosa, other ulcerative diseases of the gastrointestinal tract, some long-term complications of diabetes mellitus and certain hormone related cancers such as mammary cancer. It may also be used, not for therapeutic reasons, but to increase the rate of gain of weight of livestock.

DESCRIPTION OF THE FIGURES

FIGS. 1(A), 1(B), and 1(C) are the cDNA sequence encoding PGF.

FIGS. 2(A) and 2(B) is the amino acid sequence for PGF.

FIGS. 3(A) and 3(B) are graphs depicting the increase in weight per dose of PGF.

DETAILED DESCRIPTION OF THE INVENTION

Figure 3A:
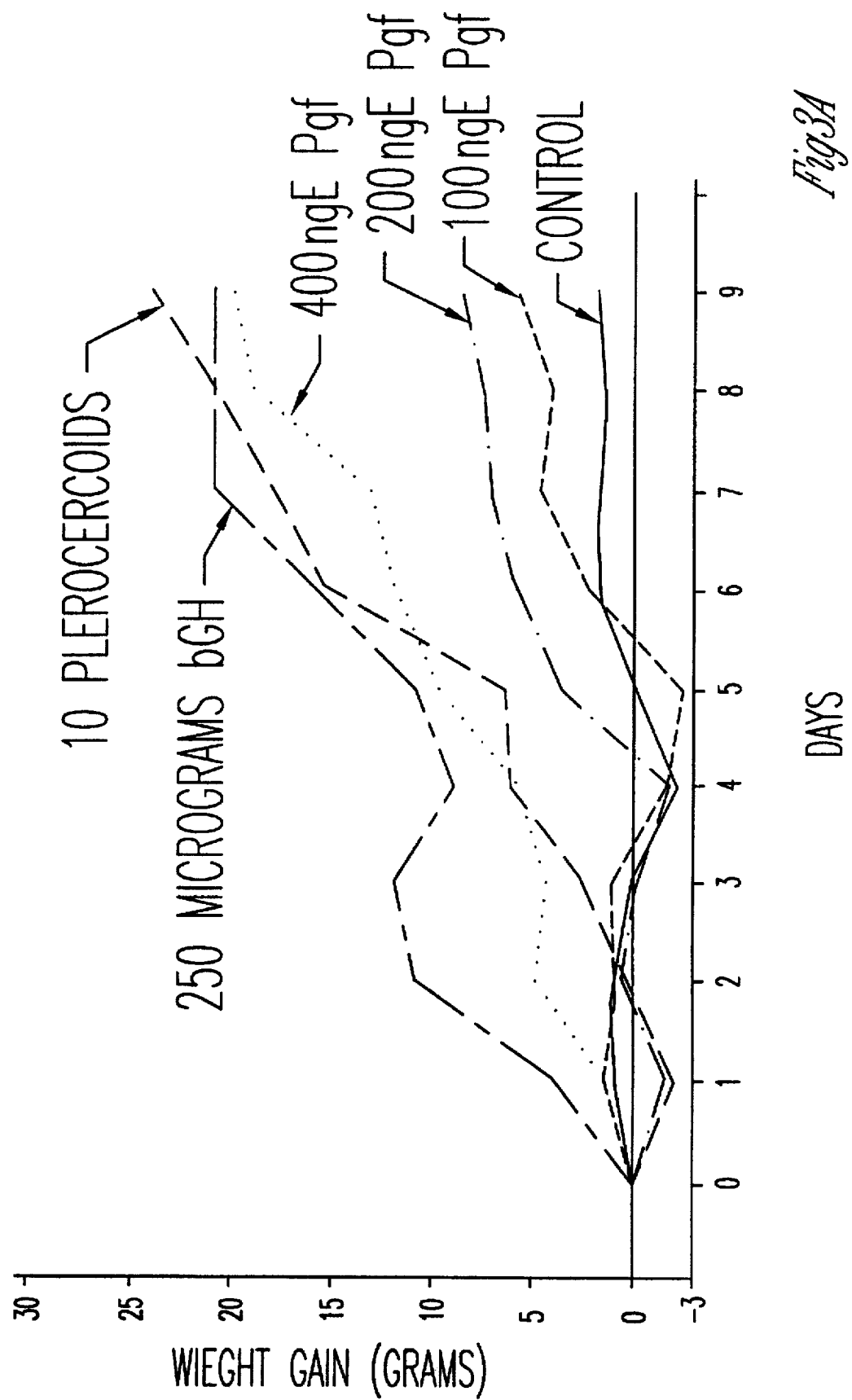

Broadly, the drug is a substance similar in biological activity to human growth hormone. It is sufficiently similar so that antibodies to human growth hormone cross react with the substance as well as with human growth hormone and certain of the biological activities regulated by this drug are also regulated by human growth hormones. However, other biological activities of human growth hormone are not caused by this drug, thus providing it with an advantage in certain therapeutic treatment. Quite unexpectedly, despite the seemingly specific similarities to HGH, the protein has an amino acid sequence which bears no homology to any known growth hormone and in fact bears 50% homology to several cysteine proteases.

A protein is defined herein as PGF if it shows PGF activity in in vitro assays, and has the biological properties enumerated below.

It: (1) is a protein; (2) is a straight chain of 216 amino acids bearing no homology to HGH; (3) has an isoeolectric point of 4.5 in contrast to the isoelectric point of human growth hormone determined by the same method which is 4.9; (4) has a molecular weight of 23,618 in contrast to 21,500 for human growth hormone when these values are determined by the same methods; and (5) has no carbohydrate groups attached to it. The drug of this application differs from human growth substance in that it does not produce resistance to insulin, is not diabetogenic, does not increase blood glucose, does not stimulate the breakdown of body fat and does not stimulate any increase in tissue receptors for the hormones prolactin or estrogen. The amino acid sequence of PGF is shown in FIG. 2 SEQ ID NO:2.

PGF is used herein to designate the foregoing protein or proteins having amino acid sequences substantially similar to that shown in FIG. 2. Of course, these definitions are not restricted to the specific sequence shown, but includes proteins which contain accidentally or deliberately induced alterations, such as deletions, additions, or exchanges of amino acid residues, so long as the biological activity, as measured by the foregoing in vitro and immunological assays, and respective anionic or cationic character at neutral pH does not change. Of course, modified forms may have slightly altered quantitative activity and specificity.

One method of obtaining this substance is to homogenize plerocercoid stage larva of tapeworm and separate the substance by separation techniques suitable for hydrophobic materials. More specifically, receptor chromatography is utilized to separate the drug from their constituents of the plerocercoids.

In using the material, dosages are considerably higher than would be used with human growth hormone. The doses are equivalent to at least 8 international units per day for more than two days. An international unit of growth hormone is that amount of growth hormone injected daily which stimulates a weight gain of 10 g (grams) (approximately 1 g/day) in a ten day hypophysectomized female rat growth bioassay. It is administered by injection.

This injection may be in multiple injections in the same day or a single injection into the subject. The injection is repeated for at least two days depending upon the disorder and these two days may either be successive days or spaced apart in time covering a period of less than one week.

More specifically, the drug has an amino acid sequence as set forth in SEQ ID NO:2 and FIG. 2. As can be seen the sequence is quite different from and shows no homology with human growth hormone.

The cDNA sequence is set forth in SEQ ID NO:1 (FIG. 1) and also bears no homology with any other growth hormone yet surprisingly bears a 50% homology to several cysteine proteases. The DNA and amino acid sequence for human growth hormone is described in "Human Growth Hormone, 1974–1981) by Choh Hao Li, *Molecular Cellular Biochemistry*, Vol. 46, pages 31–41, 1982, the disclosure of which is incorporated herein by reference.

To prepare the drug, plerocercoids of *Spirometra mansonoides* are homogenized, the protein separated and purified. The operations must take place at temperatures below 80 degrees Celsius and preferably well below 42 degrees Celsius. The separation and purification are done with the drug solubilized using a non-ionic dispersing agent. No protease inhibitor is used and the pH is maintained between 6.2 and 8.5.

More specifically, the plerocercoids of *Spirometra mansonoides* are homogenized in 25 mM (millimolars) TRIS-HCl (molar TRIS with hydrochloric acid added). After the plerocercoids are homogenized they are centrifuged in 0.3M (molar) sucrose at 5,000 gravities for 20 minutes. The membranes are then solubilized in 1 percent Triton X-100 in 25M (molar) TRIS-HCl at a pH of 7.6. Triton is used throughout the purification and assay procedures.

TRIS is a 2-amino-2-hydroxymethyl-1,3-propane-diol as described in U.S. Pat. Nos. 2,174 and 2,485,982. To obtain the TRIS-HCl, hydrochloric acid is added to the TRIS until a pH of 7.6 is reached. TRIS is sold by Sigma Chemical Co. in St. Louis, Mo.

For further purification, the homogenized substance is subjected to receptor chromatography. To prepare the receptors, a human growth hormone affinity gel is prepared and bound to fresh Affi-Gel 10. Affi-Gel 10 is a trademark for Bio-Rad Laboratories, Richmond, Calif., for an affinity gel solid support.

To purify receptors, 10 mg (milligrams) HGH (human growth hormone) which may be obtained from NIADDK, (National Institute of Arthritis, Diabetes, Digestive and Kidney), is reacted with 25 ml (milliliters) of Affi-Gel 10. Microsomes are prepared from the livers of pregnant rabbits and solubilized in 1 percent v/v (volume-to-volume) 10 mM MgCl. The solubilized proteins from one-half of each liver were chromatographed on the human growth hormone gel. It is unexpected that receptor affinity chromatography would be useful in purifying PGF, since the amino acid sequence is distinct from HGH. The difference in sequence supports a conclusion that any competitive inhibition of HGH was likely by a mechanism other than interaction with the identical highly specific HGH receptor site.

Unbound and non-specifically bound proteins were eluted by washing with 25 mM TRIS-HCl at ph of 7.6, 10 mM MgCl, and 0.1 percent Triton X-100 followed by 25 ml of 4M urea. Specifically, bound receptors were eluted with 25 mM sodium acetate at a pH of 4.5. Several cycles over the human growth hormone gel were required to remove approximately 90 percent of the binding activity. About 40 percent of the binding activity was recovered. The partially purified receptors were pooled and coupled to a solid support.

To obtain relatively pure drug, 84 ngE/mg (nanograms equivalent of an HGH standard of the eluant for each milligram) of protein was passed over the solid support at a pH of between 7.2 and 8.5 receptor gel and unbound, non-specifically bound and specifically bound proteins were eluted. The receptor gel has a binding capacity of approximately 9,000 ngE of drug. This chromatographic procedure produced increases in specific activity of more than 3,000 times the accrued protein and 88 percent of the total activity is recovered.

The entire purification procedure is carried out at a temperature lower than 80 degrees Celsius and preferably below 42 degrees Celsius. The preparation is maintained with a solubilizing agent at all times such as for example, 0.1 percent Triton X-100 or 0.2 percent CHAPS. No protease inhibitors are present during receptor affinity purification.

In using the drug, the drug is dissolved in a pharmaceutically acceptable carrier having a dispersive agent and injected in doses equivalent to approximately 1 to 10 international units per day per 45 kg (kilograms) of body weight and may be as high as 10 units. Such carriers are known in the art and can include for example saline, distilled water, aqueous solution of dextrose and the like.

As another perhaps more large scale production method the cDNA sequence encoding the proteins of the invention can be expressed in appropriate expression systems. cDNA sequences can be provided with appropriate controls suitable for any host, including bacteria, yeast, or eucaryotic cells. Exemplary control sequence DNAs and hosts are discussed below.

The recombinant PGF proteins thus produced are then purified in a manner similar to that utilized for purification of PGF from natural sources, but purification is considerably simpler, as the proteins form a much larger proportion of the starting material.

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Hosts and Control Sequences

Both procaryotic and eucaryotic systems may be used to express PGF encoding sequences; procaryotic hosts are, of course, the most convenient for cloning procedures. Procaryotes most frequently are represented by various strains of *E. coli*; however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactase (penicillinase) and lactose (lac) promoter systems (Chang, et al, *Nature* (1977) 198:1056) and the tryptophan (trp) promoter system (Goeddel, et al, *Nucleic Acids Res* (1980) 8:4057) and the lambda derived $P_L$ promoter and N-gene ribosome binding site (Shimatake, et al, *Nature* (1981) 292:128).

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the 2μ origin of replication of Broach, J. R., *Meth Enz* (1983) 101:307, or other yeast compatible origins of replication (see, for example, Stinchcomb, et al, *Nature* (1979) 282:39, Tschumper, G., et al, *Gene* (1980) 10:157 and Clarke, L, et al, *Meth Enx* (1983) 101:300) may be used. Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al, U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma, Adenovirus 2, bovine papilloma virus, or avian sarcoma viruses. The controllable promoter, hMTII (Karin, M., et al, *Nature* (1982) 299:797–802) may also be used. General aspects of mammalian cell host system transformations have been described by Axel (supra). It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

Transformations

Depending on the host cell used, transformation is done using standard techniques appropriate to such cells. The calcium treatment employing calcium chloride, as described by Cohen, S. N., *Proc Natl Acad Sci* (*USA*) 1972) 69:2110, or the rbCl2 method described in Maniatis, et al, *Molecular Cloning: A Laboratory Manual* (1982) Cold Spring Barbor Press, p. 254 and Hanahan, D., *J Mol Biol* (1983) 166:557–580 may be used for procaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777–785 may be used. Transformations into yeast may be carried out according to the method of Beggs, J. D. *Nature* (1978) 275:104–109 or of Hinnen, A., et al, *Proc Natl Acad Sci* (*USA*) (1978) 75:1929.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. Typical sequences have been set forth above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire gene sequence for genes of sizable length, e.g., 500–1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; Jay, Ernest, *J Biol Chem* (1984) 259:6311.

Synthetic oligonucleotides are prepared by either the phosphotriester method as described by Edge, et al, *Nature* (supra) and Duckworth, et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7y pmoles γ32P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl2, 6 mM DTT and 0.1–1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15–50 µl volumes under the following standard conditions and temperatures: for example, 20 mM Tris-Cl pH 7.5, 10 mM MgCl$_2$, 10 mM DTT, 33 µg/ml BSA, 10 mM–50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations are performed at 1 µM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per µg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487–6500 and Adelman, J. P., et al, *DNA* (1983) 2:183–193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

Verification of Construction

Correct ligations for plasmid construction can be confirmed by first transforming *E. coli* strain MC1061 obtained from Dr. M. Casadaban (Casadaban, M., et al, *J Mol Biol* (1980) 138:179–207) or other suitable host with the ligation mixture. Successful transformants are selected by ampicilin, tetracycline or other antibiotic resistance by using other markers depending on the mode of plasmid construction, as is understood in the art. Plasmids from the transformants are then prepared according to the method of Clewell, D. B., et al, *Proc Natl Acad Sci (USA)* (1969) 62:1159, optionally following chloramphenicol amplification (Clewell, D. B., *J Bacteriol* (1972) 110:667). Several mini DNA preps are commonly used, e.g., Holmes, D. S., et al, *Anal Biochem Acids Res* (1979) 7:1513–1523. The isolated DNA is analyzed by restriction and/or sequenced by the dideoxy nucleotide method of Sanger, F., et al, *Proc Natl Acad Sci (USA)* (1977) 74:5463 as further described by Messing, et al, *Nucleic Acids Res* (1981) 9:309, o4 by the method of Maxam, et al, *Methods in Enzymology* (1980) 65:499.

Hosts Exemplified

Host strains used in cloning and procaryotic expression herein are as follows:

For cloning and sequencing, and for expression of construction under control of most bacterial promoters, *E. coli* strains such as MC1061, DH1, RR1, C600hfl, K803, HB101, JA221, and JM101 can be used.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

EXAMPLES

The invention is illustrated by the following non-limitive examples:

General

Human growth hormone and the purified new drug (PGF) were both prepared and their effects on the growth of animals, diabetogenic characteristics and lactogenic activity compared in mammals.

Sources of Materials

The immunological grade HGH (human growth hormone) (NIADDK-HGH-I-1) was obtained from the National Pituitary Agency of NIADDK.

Triton X-100, apoprotinin, phenylmethylsulfonyl fluoride (PMSF), L-ascorbic acid, polyvinyl-pyrrolidone, Commassie Brilliant Blue R and polyethylene glycol (MW 6000) were purchased from Sigma Co., St. Louis, Mo. Affi-Gel 10, Biobeads SM-2, Bio-Rad Silver Stain and Bio-Rad protein assay kits were purchased from Bio-Rad Laboratories, Richmond, Calif.

Aquacide III (flake polyethylene-glycol) was obtained from Calbiochem-Behring, LaJolla, Calif. The anti-HGH monoclonal antibody QA68 was purchased from Wellcome Diagnostics, Dartford, England, and affinity-purified rabbit antimouse IgG was obtained from Miles Scientific, Naperville, Ill.

The DMBA and NMU were purchased from Sigma Chemical Co. (St. Louis, Mo.). Rat GH kits were generously obtained from NIADDK. Carrier-free sodium [$^{125}$I] was obtained from New England Nuclear Corp., Boston, Mass. Phosphate buffered saline (0.025M $KH_2PO_4$; 0.9 percent NaCl; pH 7.4) Polyvinylpyrrolidone (PVP) 20 percent solution was obtained from Sigma for prolonging peptide half-life. Dexamethasone sodium phosphate was obtained from Organon Inc., W. Orange, N.J., a-D(+) Glucose, 5 percent $ZnSO_4.7H_2O$), and 0.3N $Ba(OH)_2$ were obtained from Sigma.

Sources of Animals

Female C57BL/6J-ob mice weighing 40–60 g (age: 10–12 weeks old) were commercially obtained from Jackson Memorial Laboratory (bar Harbor, Me.). The 50-day old female Sprague-Dawely rats were obtained from Sasco, Inc., Omaha, Nebr.

Preparation of the HGH Affinity Gel

Tel mg of HGH was dissolved in 0.1M $NaHCO_3$, pH 8.2, and coupled to 25 ml of Affi-Gel 10 according to the instructions supplied by the manufacturer. The gel was washed and after washing and between receptor purification runs, the HGH affinity gel was stored at 4 degrees Celsius in 0.025M TRIS HCl, pH 7.6, 0.1 percent Triton X-100 (TRIS/Triton buffer) with 0.05 percent sodium azide.

Receptor Preparation

Late (250–30 days of gestation) pregnant rabbits were purchased. Hepatic microsomal membranes were isolated by differential centrifugation and receptors were solubilized and purified by affinity chromatography using a HGH-affinity column with methods similar to those of Shiu and Friesen (Shiu RPC, Friesen H. G., 1974, "Solubilization and purification of a prolactin receptor from the rabbit mammary gland", *J. Biol. Chem.*, 24–:7902), and Waters and Friesen (Waters, M. J., Friesen H. G., 1979, "Studies with anti-growth hormone receptor antibodies", *J. Biol. Chem.*, 254:6826), the disclosures of which are incorporated herein by reference.

The microsomes from approximately one-half of each rabbit liver were processed at one time. For each run the microsomes were diluted with 25 mM TRIS-HCl, pH 7.6, 1 percent (vol/vol) Triton X-100, 10 mM $MgCl_2$ in a ratio to give a protein concentration of approximately 10 mg/ml. The microsomal pellet was dispersed in the Triton-containing buffer with five strokes of a teflon Potter Elvehjem homogenizer (Bellco, Inc., Vineland, N.J.) and then mixed gently at room temperature for 30 minutes.

The mixture was then centrifuged at 105,000 g for 90 minutes. The supernatant was decanted and most of the Triton X-100 was removed by adding 150 mg of Biobeads SM-2 for each ml of the soluble fraction and then mixing on a Roto-Torque (Cole-Palmer Co, Chicago, Ill.) in the cold room for 90 minutes. The Biobeads were removed by filtration and the soluble proteins were frozen at −70 degrees Celsius until used.

Purification of the Solubilized Receptors

Solubilized receptors from the livers of six pregnant rabbits were chromatographed over the HGH affinity gel. For each chromatographic run approximately 90 ml (one-half of a liver) of solubilized microsomal proteins were processed. Protease inhibitors were added to the mixture to give a final concentration of 0.3 mM PMSF, and 5000 Kallikrein inactivating units/ml (Apopritinin). The solubilized membranes were added to HGH-affinity gel and the gel slurry was gently mixed by end over end rotation at room temperature for two hours.

After the two hour incubation, the procedure was transferred to the cold room and the slurry was poured into a 26×40 cm (centimeter) chromatographic column with flow adaptors (Pharmacia Fine Chemicals, Uppsala, Sweden) and allowed to settle. The unbound protein was collected and the gel was then slowly washed (usually overnight) with approximately 100 column volumes of TRIS/Triton buffer. On some occasions, the column was washed only until the absorbence at 280 nm of the wash returned to baseline (void volume plus 2–3 additional column volumes of TRIS/Triton). In all cases after the TRIS/Triton buffer wash, the column was washed with one column volume of 4M urea to remove nonspecifically bound materials.

Following the urea wash, the gel was washed with a minimum of 4 volumes of the TRIS/Triton buffer. To elute specifically bound receptors, one column volume of 23 mM sodium acetate pH 4.5 containing 0.1 percent Triton X-100 was applied directly to the top of the column. The pH of the subsequent fractions was monitored and immediately adjusted to pH 7.6 with one M $NaHCO_3$. Fractions were frozen at −70 degrees Celsius until assayed. An additional 50 mls of TRIS/Triton buffer were passed over the gel before one column volume of 5M $MgCl_2$ was applied to remove any bound material remaining. The gel was then extensively washed with TRIS/Triton buffer and was ready for immediate reuse or storage.

The entire procedure was then repeated with the original void volume (unbound solubilized microsomal protein) from the first run. Therefore, each half of the rabbit liver microsomes was passed over the HGH-affinity gel twice.

Preparation of Receptor Affinity Gel

Purified receptors from all six rabbits were pooled and poured into dialysis tubing which had been boiled for 30 minutes in 5 mM EDTA. The pooled receptors were concentrated to a volume of about 50 ml with flaked polyethylene glycol (Aquacide III, Calbiochem, La Jolla, Calif.). The concentrated receptors were transferred to fresh dialysis tubing and dialyzed against 60 volumes (3 changes) of 0.M $NaHCO_3$ at a pH of 8.5.

After dialysis the receptors were transferred to a flask containing 25 mls of Affi-Gel 10 and coupled as described for the HGH-affinity gel. After coupling the receptor, gel was poured into q chromatographic column (26×40 cm) and washed with a sequence of: one 1 (liter) of 25 mM TRIS-HCL, pH 7.6, 10 mM $MgCl_2$, 0.1 percent Triton X-100 (TRIS/Triton), one 1 of 0.1M $NaHCO^3$, one 1 of TRIS/Triton, 0.5 l of 8M Urea in TRIS/Triton, one 1 TRIS/Triton, 0.5 l of 5M $MgCl_2$ in TRIS/Triton and one 1 of TRIS/Triton. The receptor affinity gel was stored at 4 degrees Celsius in TRIS/Triton buffer with 0.05 percent sodium azide.

Preparation of PGF for Affinity Chromatography

All stages of the life-cycle of *Spirometra mansonoides* are maintained in the laboratory on a large scale by methods based on those described in Mueller, J. F. (1966), "The laboratory propagation of *S. mansonides*, (Mueller, 1935); as an experimental tool, "VII. Improved techniques and additional notes on the biology of the cestode", *J. Parasitol*, 52:437, the disclosure of which is incorporated herein by reference.

Plerocercoids were homogenized with a conical glass tissue homogenizer (Bellco Inc., Vineland, N.J.) in 25 mM TRIS-HCL pH 7.6 with 0.3M sucrose in a ratio of 1 g worms to 5 ml of buffer. The homogenate was filtered through cotton gauze and centrifuged at 12 g (gravities) for five minutes. A two phase pellet was obtained, the lower phase consisted of calcareous corpuscles which were discarded. The upper phase consisted of tissue debris which was saved with the supernatant. The low speed centrifugation was repeated twice.

The homogenate was then centrifuged at 5,000×g for 20 minutes at 5 degrees Celsius. The supernatant was discarded and the pellet was dispersed in 25 mM TRIS-HCL pH 7.6, 1 percent Triton X-100 (1 ml of solubilizing buffer per gram of original worm mass) with five strokes of a Teflon-glass homogenizer (Bellco Glass Co.) and solubilized for 30 minutes at room temperature with gentle stirring. The mixture was centrifuged at 105,000 g for 90 minutes at 5 degrees Celsius.

The soluble fraction was added to Biobeads SM-2 manufactured by Bio-Rad treated to receive Triton in a ratio of 300 mg of beads/ml of solubilized solution and gently shaken at 5 degrees Celsius for 90 minutes. This procedure was employed to remove most of the Triton X-100, Holloway, P. W., 1973, "A simple procedure for removal of Triton X-100 from protein samples", *Anal. Biochem.*, 53:304, the disclosure of which is incorporated herein. The solubilized material (crude PGF) was separated from the Biobeads by filtration over a glass wool filter.

Receptor Purification

A preliminary experiment to determine the most productive and efficient method for purifying receptors was conducted. The solubilized microsomal proteins from one-half of a rabbit liver were chromatographed over the HGH-affinity gel. The unbound material was subjected to an additional chromatographic cycle. Most of the specific binding was associated with the fractions which eluted in the sodium acetate pH 4.5 washes.

Since 250 ug/tube of the unbound protein from the second pass specifically bound only 3 percent of the $[^{125}I]$ HGH a third passage over the column was considered not to be warranted. Therefore, solubilized microsomes from each half of the livers of the remaining rabbits were passed over the HGH column twice.

After the liver microsomal receptors had been solubilized and purified over the HGH-affinity gel, total recovery of protein and the binding activity of the specifically eluted fractions were determined. The data in Table 1 show that less than a tenth of one percent of the total protein was recovered but that the binding activity (expressed as percent specific binding/ug (microgram) protein of the purified receptors was significantly increased.

As shown in Table 1, the total protein was from 601 g of rabbit liver (6 livers). Microsomes were prepared and solubilized as described above. The protein values for the microsomes and Triton-solubilized microsomes was the sum obtained from the six independent liver preparations. The total protein for the affinity-purified receptors was obtained by measuring the protein concentrations in a pool of the concentrated receptors from all six livers.

Specific binding was determined as the difference between total binding and non-specific binding and was expressed as a percent of the total cpms of $[^{125}I]$ HGH added to the assay tubes. The data given in this column was obtained by dividing the percent specific binding for each preparation by the total amount of protein in the assay tube. For the microsomes and Triton-solubilized microsomes, 250 ug of protein was added to the assay tubes and the data given as the mean of independent assays from each of the six preparations, the data for the affinity-purified receptors was obtained in a single binding assay using 2 ug of protein per tube from pooled and concentrated receptors from all six livers.

TABLE 1

Affinity Purification of Rabbit Liver Receptors for HGH

| | Total Protein Purification | Recovery | Specific Binding/ug Protein % | Fold |
|---|---|---|---|---|
| Microsomes | 13.67 g | 100.00% | 0.13 | 1.0 |
| Triton-Solubilized Microsomes | 10.16 g | 74.00% | 0.15 | 1.2 |
| Affinity-purified Receptors | 11.82 mg | 0.09% | 21.92 | 169.0 |

Fold purifications were obtained by dividing the specific binding/ug of purified receptor protein by that obtained with the microsomes. Receptors were purified over an HGH-affinity column as described above.

The partially-purified receptors prepared from all six rabbit livers were pooled, and concentrated for coupling with 20 ml of Affi-Gel 10. Coupling was accomplished in the cold room overnight. The gel was poured into a conical tube and allowed to settle, the unbound receptor protein in the supernatant was aspirated and mixed with 5 ml of fresh Affi-Gel 10. Assay of the protein remaining in the uncoupled fraction after the second coupling showed that less than 1 mg of protein did not bind the Affi-Gel 10. Therefore, the 25 ml receptor affinity gel was assumed to contain 11.1 mg of purified receptor protein.

The ability of the receptor-affinity gel to bind HGH was determined by mixing $[^{125}I]$ with a small aliquot (250 ul) of the receptor-gel. A distinct peak of $[^{125}I]$ HGH was specifically eluted by the sodium acetate, pH 4.5 wash. Therefore, it was concluded that the receptors coupled to Affi-Gel 10 retained the ability to specifically bind HGH.

Binding Assays

The ability of the receptors to specifically bind $[^{125}I]$ HGH was monitored for each step of the procedure. Binding of $[^{125}I]$ HGH membrane-bound receptors was carried out by the methods of Tsushima and Friesen (Tsushima T., Friesen H. G., 1973, "Radioreceptor assay for growth hormone", *J. Clin. Endocrinol Metab.*, 27:334, (the disclosure of which is incorporated herein by reference) except that the incubation times were overnight (15–18 hours) at room temperature assay. However, except for the addition of 0.1 percent Triton X-100 to maintain solubility of the receptors and polyethylene glycol (PEG) 6000 to precipitate the hormone-receptor complexes, conditions for binding assays with soluble receptors and affinity-purified receptors were the same as with membrane bound receptors.

For routine monitoring of $[^{125}I]$HGH binding in particulate microsomes and solubilized microsomes, 250 ug of protein from each preparation was included in each of the duplicate incubation tubes. Specific binding was the amount of [$^{125}$I]HGH bound to membranes, solubilized membranes or affinity-purified receptors after subtracting the [$^{125}$I]HGH bound (non-specific binding) in the presence of an excess of unlabeled HGH (1 ug/ml). A Beckman 5,5000 Gamma Counting System (Beckman Institute, Fullerton, Calif.) with a counting efficiency for [$^{125}$I] of 70 percent was used.

Protein Assays

All protein determination was accomplished with the Bio-Rad Protein Assay kit with bovine gamma globulin as the standard. Depending on the protein concentration of the samples, either the standard assay procedure (range 20–140 g protein) or the microassay procedure (1–20 ug protein) was used.

Example 1

Preparation of Drug Receptor Chromatography

Plerocercoids were homogenized with a conical glass tissue homogenizer (Bellco, Inc., Vineland, N.J.) in 25 mM TRIS-HCL pH 7.6 with 0.3M sucrose in a ratio of 1 g worms/5 ml of buffer.

The homogenate was filtered through cotton gauze and centrifuged at 12 g for five minutes. A two-phase pellet was obtained, the lower phase consisted of calcereous corpuscles, (VonBrand, T., 1973, "Biochemistry of Parasites", ed. 2, Academic Press, New York, p. 7, (the disclosure of which is incorporated herein by this reference) which were discarded, the upper phase consisted of tissue debris which was saved with the supernatant.

The low speed centrifugation was repeated twice. The homogenate was then centrifuged at 5,000×g for 20 minutes at 5 degrees Celsius. The supernatant was discarded and the pellet was dispersed in 25 mM TRIS-HCL pH 7.6, 1 percent Triton X-100 (1 ml of solubilizing buffer per gram of original worm mass) with five strokes of a Teflon-glass homogenizer (Bellco Glass Co.) and solubilized for 30 minutes at room temperature with gentle stirring.

The mixture was centrifuged at 105,000 g for 90 minutes. The soluble fraction was added to Biobeads SM-2 in a ratio of 300 mg of beads/ml of solubilized solution and gently shaken at 5 degrees Celsius for 90 minutes. This procedure was employed to remove most of the Triton X-100 (Holloway, P. W., 1973, "A simple procedure for removal of Triton X-100 from protein samples", Anal. Biochem., 53:304, (the disclosure of which is incorporated herein by this reference). The solubilized material (crude PGF) was separated from the Biobeads by filtration over a glass wool filter.

Quantitation of PGF in the crude preparation and in fractions from the receptor affinity column was based on binding activity in a radioreceptor assay (RRA) using rabbit hepatic membrane receptors [$^{125}$I]HGH and HGH. The assay was conducted as previously described except an overnight (16–18 hour) incubation at room temperature was used and Triton X-100 (0.1 percent) was present in the assay tubes. Activity of PGF is expressed as nanogram equivalents (ngE) of the HGH standard.

Receptor affinity chromatography of crude PGF was conducted under conditions essentially the same as those described for the purification of the receptors on the HGH affinity column except that no protease inhibitors were used and the pH of the specifically eluted material was adjusted to pH 7.6 with a saturated TRIS solution. For recycling, the gel was washed extensively after each run with the TRIS/Triton buffer followed by one column volume of 5 m MgCl$_2$ and again washed extensively and stored in TRIS/Triton buffer plus 0.05 sodium oxide.

Polyacrylamide gel electrophoresis (PAGE) of the affinity-purified PGF in SDS containing gels was conducted. The procedures used were those originally described by Laemmli (Laemmli, U.K., 1970, "Cleavage of structural proteins during the assembly of the head of bacterophage t3", Nature, 227:680, (the disclosure of which is incorporated by this reference).

Protein standards (Bio-Rad) ranging in molecular weight from 92,500 to 14,400 daltons and HGH were co-electrophoresed with the affinity-purified PGF. The molecular mass of the proteins in the stained bands of the affinity-purified PGF was estimated based on regression analysis of the relative mobilities (rf) by the molecular weight program in a DP-5500 Data Reduction System (Beckman, Colo.).

Example II

Preparation of Drug Receptor Chromatography

Active PGF from plerocercoids was obtained by solubilization of whole plerocercoids in the non-ionic detergent Triton X-100 as described in the aforementioned publication of Phares (1984) the disclosure of which is incorporated herein. In a typical preparation, a membrane fraction was separated from the other components of the homogenized plerocercoids by centrifugation at 5,000 g for 20 minutes and the membranes were solubilized. Usually 12–20 g (wet weight) of plerocercoids were processed and for each 1 g of plerocercoid, approximately 1 ml of crude solubilized PGF was obtained.

The data in Table 2 describe the activity and protein concentrations of six independent preparations. The crude PGF was obtained from plerocercoid membranes, were prepared and solubilized in 1 percent vol/vol Triton X-100 as described above. The values given in Table 2 are the mean for ±SE for six independent preparations.

TABLE 2

| RECEPTOR AFFINITY PURIFICATION OF PGF | | |
|---|---|---|
| | Crude PGF | Affinity Purified PGF |
| Binding Activity (ngE/ml) | 915 ± 113 N = 6 | 1512 ± 84 N = 9 |
| Protein Concentration (mg/ml) | 7.6 ± 0.5 | 0.013 ± 0.003 |
| Specific Activity (ngE/mg) | 118.5 ± 13.6 | 123.730 ± 12,064 |
| Fold Purification | 1 | 1,044 |

The affinity-purified PGF shown in Table 2 was obtained from chromatography of the crude PGF over an HGH receptor column as described above. The values presented are the mean ±SE for the peak fractions of nine separate chromatographic runs. Quantitation of PGF was based on competitive displacement of [$^{125}$I]HGH from rabbit liver microsomes in an RRA. The amount of PGF was expressed as nanogram equivalents (ngE) of the HGH standard. The difference in specific activity (ngE/mg protein) between the crude and affinity-purified PGF was used as a measure of the increase in purity.

The first figure represents elution profiles in terms of binding activity of a representative affinity chromatographic run in which 8,400 ngE of PGF in 12 mls was mixed with the receptor gel and chromatographed as described above. No detectable PGF activity was found by RRA in the unbound fractions nor in the non-specifically bound (urea wash) fraction. A total of 7,767 ngE (92 percent) of the PGF applied to the column was recovered.

By combining differential centrifugation, solubilization, with Triton X-100 and receptor-affinity chromatography, PGF was purified 1,100–1,500 fold. Table 2 summarizes data from nine separate affinity purifications of PGF.

Example III

In Vitro Test

Quantitation of PGF in the crude preparation and in fractions from the receptor affinity column was based on binding activity in a radioreceptor assay (RRA) using rabbit hepatic membrane receptors, [$^{125}$I]HGH and HGH. The assay was conducted as described in (Tsushima T., Friesen, H. G., 1973, "Radioreceptor assay for growth hormone", *J. Clin. Endocrinol Metab.*, 27:334, the disclosure of which is incorporated herein by this reference, except an overnight (16–18 hour) incubation at room temperature was used and Triton X-100 (0.1 percent) was present in the assay tubes. Activity of PGF is expressed as nanogram equivalents (ngE) of the HGH standard.

Example IV

In Vitro Test

Affinity-purified PGF, HGH and molecular weight standards were electrophoresed in a 15 percent polyacrylamide gel in the presence of SDS and 2-Mercaptoethanol. When the gel was stained by only Commassie Brilliant Blue, a single stained band with molecular weight of 27,500 daltons was resolved. The gel was then stained with silver for greater resolution.

Affinity-purified PGF was not homogenous and contained three stained bands. Molecular weights were calculated based on the rfs of the bands and comparison to a standard curve based on the mobilities (rf) of the standards. The molecular weight of the three bands corresponded to 27.5K, 22K and 16.7K respectively. The HGH band corresponded to a molecular weight of 22K in this system.

Example V

In Vitro Test

Affinity-purified PGF and HGH were subjected to PAGE as described above with SDS in 15 percent gels both in the presence (reducing conditions) and absence (non-reducing conditions) of 2-mercapto-ethanol. Protein bands were electrophoretically transferred to nitrocellulose sheets with a Trans Blot System (Bio-Rad, Inc., Richmond, Calif.). The nitrocellulose sheets were washed in phosphate-buffered saline (PBS) 0.15M NaCL, 1.5 mM $KH_2PO_4$, 0.8 mM $Na_2HPO_4$, 2.7 mM KCL pH 7.4) containing Tween 20 (0.05 percent volume/volume) for six hours to block non-specific binding to the paper.

The blots were incubated overnight in PBS-Tween 20 containing the anti-HGH mAb QA68 (100 ul of ascites fluid diluted in 20 ml of PBS-Tween 20). The sheets were washed with three changes of 100 ml each of PBS-Tween 20 before incubating the sheets with [$^{125}$I]-labeled rabbit anti-mouse IgG, ($3\times10^6$ cpm/gel lane). The immunoblots were dried and the bands were developed by autoradiography.

The anti HGH mAb identified HGH, the 22K protein bands from partly purified PGF and the 16.7 K protein band from the partly purified PGF.

Example VI

Hypophysectomized Rat Weight Gain

The ability of the affinity-purified PGF to stimulate growth was determined in a ten-day Hx rat weight gain bioassay. Male Hx rats (120 g) (Hormone Assay Labs, Chicago, Ill.) were received ten days post-surgery. They were allowed free access to Wayne Lab Blox and drinking water supplemented with ascorbic acid (2 mg/l). The light cycle (12 hours of light and 12 hours of darkness) lights on at 0700 hour and temperature (22.0±0.5 degrees Celsius) were automatically controlled. None of the Hx rats gained more than 5 g during the two weeks prior to the initiation of the assay.

Five or six rats were included in each of the experimental groups and the control group consisted of ten Hx rats. The rats of one group were infected with 15 plerocercoids each by subcutaneous injection on the first day of the experiment. The rats in all the other groups received either affinity-purified PGF (100–400 ngE/day), bovine GH (bGH 250 ug/day) or saline. Each of the injected preparations was suspended in polyvinylpyrrolidone (PVP) in a manner to give a final concentration of 10 percent PVP. The animals were injected subcutaneously with 1 ml of the appropriate preparation each day for nine days. Body weight (including day 10) were recorded daily.

The ability of daily injections of affinity-purified PGF to stimulate growth of Hx rats was compared to that of injections of bGH (250 ug/day) or a subcutaneous infection with 25 plerocercoids for each rat.

A pool of several receptor affinity-purified preparations of PGF with an activity of 1,700 ngE/ml was diluted in a manner to give aliquots containing 400, 200 and 100 ngE/ 0.5 ml which were injected daily into Hx rats for nine days.

The graph at FIGS. 3(A) and 3(B) shows that PGF stimulated a dose dependent (r=0.98) increase in weight and that daily injections of 400 ngE of PGF stimulated a total weight gain not statistically different from that produced by 250 ug of bGH each day or infections with 25 plerocercoids per rat. These results show that the material purified over the receptor affinity gel and assayed by the rabbit liver RRA contains the growth promoting component produced by the plerocercoids.

The fact that the mobility of PGF in the non-reduced gel was essentially the same as in the reduced gel suggests the possibility that PGF may not contain one or both of the two disulfide bonds which are found in HGH. Alterations are known to be apparent in the molecular weight of proteins by reduction of disulfide bonds.

Example VII

Test for Diabetogenicity in Obese Mouse

The drug used was prepared by solubilization (1 percent Triton X-100) of plerocercoid membranes, and had an activity of 1,227 nanogram equivalents (ngE)/ml of an HGH standard as determined in a rabbit liver membrane RRA as described above.

To determine an effective dose range for use in the ob/ob mice, the ability of daily injections of the drug (12.5 to 100 ngE) to simulate growth of phenotypically normal (C57BL/6J-ob) mice was assessed in a ten-day weight gain assay. The mice were divided into groups of 5 to 7 mice.

In the first treatment all injections contained 10 percent PVP final concentration. The mice were subcutaneously injected with PBS (phosphate buffered saline) for three days. On the fourth day, the mice were subcutaneously injected with 2 ug dexamethasone. The mice were fasted for a period of at least 8 hours (8–10 hours).

Fasting blood samples (25 ul) were collected from the mice in plastic micro test tubes by retrosinus plexus orbital puncture using very narrow capillary tubes (zero time). The mice were injected i.p. with glucose (1 mg/kg body weight). Blood samples 25 ul) were collected in plastic micro test tubes at intervals of 15, 30, 60, 90, 120 and 180 minutes and placed on ice.

To all the 25 ul blood samples, 75 ul of $ZnSO_4$ solution and 75 ul of $Ba(OH)_2$ solution were added to precipitate the blood proteins and cells. The samples were centrifuged and the clear supernatant was collected. Glucose content was determined in triplicates by glucose oxidase method using the Beckman Glucose Analyzer.

In the second treatment, the mice were allowed to rest for 7–10 days. To test for the effects of HGH (100 ug/day) or various concentrations of PGF (50–200 ngE/day), mice were subcutaneously injected with the test dose in 10 percent PVP for three days. The same procedure of treatment no. 1 described above was followed for the remainder of the procedure. Each mouse served as its own control, i.e., the PBS treatment vs. sample test-dose treatment. The data for each treatment group was combined for statistical analysis. The glucose tolerance test was repeated at least once with the same group of mice.

Diabetogenic activity was assessed in female ob/ob mice as described by Reagan (Diabetes 27:773, 1978). Injections of PGF produced a dose-related weight gain in the normal mice (r=0.83) and 25 ngE of PGF stimulated a response which was significantly greater (p>0.01) than controls and equivalent to the gain produced by 10 ug of bovine GH/day (1.4 IU/mg). Five doses of PGF (50–200 ngE/day) were tested for diabetogenicity and compared to 100 ug/day of HGH (2.2 IU/mg).

Example VIII

Regression of Induced Tumors

Induction of Mammary Tumors and PGF-Treatment

Tumors were induced in one experiment by intragastric feeding of 20 mg of DMBA in 1 ml of peanut oil to 50-day old female Sprague-Dawely rats. In a separate group of 50-day old female Sprague-Dawely rats, mammary tumors were induced by two intravenous injections of MNU (5 mg/100 g of body weight) given one week apart.

When palpable tumors began to appear, they were inspected and measured twice each week. Tumor sizes were derived from the product of the lengths of the two major axes measured with a caliper. When multiple tumors were present in a rat, the growth pattern of each was considered separately.

Approximately 14 weeks after the DMBA or NMU treatments, half of the rats in each experiment were injected subcutaneously in the nuchal area with 25 plerocercoids. This form of PGF treatment has been shown to provide a constant infusion of PGF and to stimulate body growth, reduce serum GH, and suppress tissue receptors for PRL and estrogen. During the three weeks of PGF treatment, all the rats were weighed twice each week.

Serum GH

At the end of the three-week experimental period, the rats were killed by decapitation and serum was separated for GH measurement. Rat GH concentrations were determined in a double antibody radioimmunoassay (RIA) using rhesus monkey antiserum to rGH and reference rGH provided by NIADDK. Goat antimonkey globulin (Calbiochem-Behring, La Jolla, Calif.) was used as the second antibody. The radioactivity in the rGH RIA tubes was counted and the data was analyzed by logic-log regression in a Beckman Gamma Counter equipped with a DP Data Reduction System (Beckman Instruments, La Jolla, Calif.). The intra-assay coefficient of variation using a single preparation of normal rat serum was 6 percent. The minimal detectable dose was 0.5±0.2 ng/ml and this value was used for samples with rGH below the detectable limit.

Statistical Methods

All data is presented as the mean±SE. Statistical comparison of the groups was accomplished by Student's t test or by the Chi square test.

Treatment of the rats with PGF was initiated approximately 14 weeks after DMBA or NMU treatment. As shown in Table 3, both the DMBA- and NMU-injected rats exposed to PGF gained more than three times as much weight during the three-week treatment period than did their respective controls. The accelerated weight gain in the rats treated with PGF was associated with dramatic reductions in serum GH concentrations.

TABLE 3

Effects of Three Weeks of PGF-Treatment on Body Weight Gain and Serum GH Concentrations in Female Rats Bearing Mammary Tumors Induced by DMBA or NMU

| Group | (n) | Total Weight Gain (g) | Serum GH (ng/ml) |
|---|---|---|---|
| DMBA (Control) | 10 | 6.8 ± 1.4 | 60.1 ± 11.8 |
| DMBA (PGF) | 10 | 19.6 ± 3.5 | 13.1 ± 1.7 |
| NMU (Control) | 9 | 7.5 ± 1.5 | 72.5 ± 10.3 |
| MNU (PGF) | 9 | 24.1 ± 3.7 | 7.8 ± 1.8 |

At the time the DMBA-injected rats were entered into the hormonal manipulation phase of the experiment (PGF-treatment) as shown in Table 3 and 5, the control rats had an average of 2/1 tumors each which had a mean surface area of 3/7±0.6 $cm^2$ compared to 2.2 tumors which a mean surface area of 4.1±0.7 $cm^2$ in the PGF-treated rats. There was no statistical difference in these values.

If tumor growth after initiation of PGF-treatment is subdivided into regressing (>30 percent of initial size), static (between >39 percent and >10 percent of initial size) or growing (<10 percent increase over initial size) it can be seen from the data in Table 4 that almost 60 percent of the tumors in the PGF-treated group regressed while two-thirds of the control tumors continued to grow.

Very similar results were obtained with mammary tumors induced by NMU as shown in Tables 3 and 4. In these rats, the mean initial size of the tumors was 5.8±1.5 $cm^2$ for the control animals (1.2 tumors/rat) and 4.4±1.2 $cm^2$ (N.S.) for those in the group which received PGF (1.7 tumors/rat). Almost three-fourths of the control NMU-induced tumors continued to grow while approximately two-thirds of the tumors in PGF-treated group were at least 30 percent smaller at the end of the three weeks of treatment.

TABLE 4

Response of NMU-induced Mammary Tumors to Three Weeks of PGF Treatment

| Group | Total No. of Tumors | Tumor Growth (% of Total) | | |
|---|---|---|---|---|
| | | Regressing | Static | Growing |
| Control N = 9 | 11 | 9.1 | 18.2 | 72.7 |
| PGF N = 9 | 15 | 66.7 | 6.7 | 26.7 |

TABLE 5

Response of DMBA-induced Mammary Tumors to Three Weeks of PGF Treatment

| Group | Total No. of Tumors | Tumor Growth (% of Total) | | |
|---|---|---|---|---|
| | | Regressing | Static | Growing |
| Control N = 9 | 21 | 4.8 | 33.2 | 66.6 |
| PGF N = 9 | 22 | 59.0 | 18.2 | 22.7 |

From the above description, it can be understood that the novel drug of this invention and the method of making and using it have several advantages over the prior art human growth hormone, such as: (1) it stimulates growth without being diabetogenic or having other harmful effects; (2) it can be obtained from sources other than the human pituitary; and (3) it can be administered in larger doses and more frequent doses than human hormone.

Example IX

Molecular Characterization of PGF (Plerocercoid Growth Factor)

Considering the ability of PGF to competitively inhibit binding of HGH to its receptors and to mimic biological actions believed to be unique to HGH, one of skill in the art would assume that PGF and HGH must share significant structural homology. Quite surprisingly this was not the case. The amino acid sequence of PGF was determined from the cDNA and is shown in FIGS. 1A–1C SEQ ID NO:1.

The sequence of PGF was characterized by isolating messenger RNA (mRNA) from plerocercoids, preparing a complementary DNA (cDNA) library, designing a probe to specifically identify the cDNA encoding PGF, amplifying the cDNA for PGF, sequencing the cDNA SEQ ID NO:1 and thus deducing the full-length amino acid sequence of the precursor and mature forms of the PGF protein SEQ ID NO:2.

More specifically limited trypsin digestion of the purified 27.5 kD protein was necessary as the amino-terminal of the 27.5 kD protein was blocked and unavailable for direct sequencing. Several peptide fragments were sequenced, none of which showed any homology to GH. However, sequences were selected and used to design oligonucleotide probes to identify the cDNA for the 27.5 kD protein. A plerocercoid cDNA library was constructed with bacteriophage lambda gt11 DNA in E. coli. The polymerase chain reaction using synthetic oligonucleotides was performed to amplify cDNA for the 27.5 kD protein. A sequence of 651 bases of the cDNA was obtained and is shown in FIGS. 1A–1C SEQ ID NO:1. The amino acid sequence of the mature 27.5 kD plerocercoid protein is shown in FIGS. 2A–2B SEQ ID NO:2. A computer search of both nucleotide and peptide sequence data bases revealed no homology to any known growth hormone. However, there was significant (≈50%) homology to several cysteine proteinases. Highest homologies were to the mammalian lysosomal enzymes, cathepsin L and cathepsin S. Comparison of consensus sequences of two highly conserved regions of cysteine proteinases (North et al., 1990) to the sequence of the 27.5 kD plerocercoid protein shows total identity to one of the highly conserved regions and only one amino acid difference in the other region. The sequences of these two conserved regions in the 27.5 kD protein and in human cathepsin L are 100% identical.

Subsequent studies confirmed that the 27.5 kD plerocercoid protein is a neutral cysteine proteinase (Braun et al., 1989). Confirmation was based on substrate and inhibitor specificity, activation by thiol-containing compounds and zymogram analysis. The plerocercoid proteinase was very active against a collagen substrate and the 27.5 kD proteinase is glycosylated. As the proteinase is membrane-associated and released into the environment of plerocercoids, and is very active against collagen, an important function must be in tissue penetration to allow rapid migration of plerocercoids.

The interaction of HGH with its receptors has recently been shown to be much more complex than the concept that one molecule of hormone binds to one receptor molecule to initiate a hormonal signal. Contrary to early studies that reported a single binding site in HGH, recent work clearly indicates that each HGH molecule has two distinct non-overlapping binding sites which enable one molecule of HGH to dimerize two identical receptors by a sequential binding mechanism (Cunningham et al., 1989). Furthermore, mutants of HGH which are able to bind one receptor, but are unable to induce receptors dimerization, are biologically inactive (Cunningham and Wells, 1989). It is possible that a highly specific "lock and key" interaction of GH with its receptor is less important than dimerization of two receptors for induction of GH-like responses.

Without wishing to be bound by any theory it is postulated that PGF Stimulates HGH-like responses, not through precise molecular mimicry of HGH, but by inducing dimerization of GH receptors and acting as a potent hormonal agonist. The distinct differences between some biological actions of PGF and HGH described above support the concept of non-identical mechanisms for receptor activation.

Example X

Baculovirus Expression System for Production of PGF

A baculovirus expression system has been used to obtain and produce PGF. The baculovirus expression system takes advantage of several facts about polyhedrin protein: (1) that it is expressed at very high levels in infected cells, constituting more than half of the total cellular protein late in the infectious cycle; (2) that it is nonessential for infection or replication of the virus, meaning that the recombinant virus does not require any helper function; and (3) that viruses lacking the polyhedrin gene have a plaque morphology that is distinct from that of viruses containing the gene. Recombinant baculoviruses are generated by replacing the polyhedrin gene with a foreign gene through homologous recombination. In this system, the distinctive plaque morphology provides a simple visual screen for identifying the recombinants.

To produce a recombinant virus that expresses the gene of interest, the gene is first cloned into a transfer vector. Most baculovirus transfer vectors contain the polyhedrin promoter followed by one or more restriction enzyme recognition sites for foreign gene insertion. Once cloned into the expression vector, the gene is flanked both 5' and 3' by viral-specific sequences. Next, the recombinant vector is transfected along with wild-type viral DNA into insect cells. In a homologous recombination event, the foreign gene is inserted into the viral genome and the polyhedrin gene is excised. Recombinant viruses lack the polyhedrin gene and in its place contain the inserted gene, whose expression is under the control of the polyhedrin promoter.

Homologous recombination between circular wild-type DNA and the recombinant plasmid DNA occurs at a low frequency (typically 0.2% to 5%). However, linearization of wild-type baculovirus DNA before cotransfection with plasmid DNA increases the proportion of recombinant virus to ~30% (Kitts et al, 1990, "Linearization of Baculovirus DNA Enhances the Recovery of Recombinant Virus Expression Vectors", *Nucl. Acids Res.*, 18:5667-5672). If the DNA is linearized such that an essential portion of the 1629 open reading frame (ORF) downstream from the polyhedrin gene is deleted, 85% to 99% of the viruses obtained by cotransfection with a plasmid vector that complements the deletion express the heterologous gene (Kitts and Possee, 1993, "A Method for Producing Recombinant Baculovirus Expression Vectors at High Frequency", *BioTechniques*, 14:810-817). Two companies (Pharmingen and Clontech) market linear AcMNPV DNA containing such a deletion.

Once a virus stock is obtained after cotransfection, it is necessary to purify recombinant virus by plaque assay so the recombinant virus can be identified. Limiting dilution can also be used (O'Reilly et al, 1992, "Baculovirus Expression Vectors", W. H. Freeman and Company, New York. One of the advantages of this expression system is a visual screen allowing recombinant viruses to be distinguished. As mentioned above, the polyhedrin protein is produced at very high levels in the nuclei of infected cells at late times after viral infection. Accumulated polyhedrin protein forms occlusion bodies that also contain embedded virus particles. These occlusion bodies, up to 15 um in size, are highly refractile—i.e., they have a bright, shiny appearance that is readily visualized under the light microscope. Cells infected with recombinant viruses lack occlusion bodies. Thus, when the virus is plaqued onto Sf9 (Spodoptera frugiperda) cells, plaques can be screened for the presence (indicative of wild-type virus) or absence (indicative of recombinant virus) of occlusion bodies. Recombinant viruses can also be identified by DNA hybridization and polymerass chain reaction (PCR) amplification.

Post-Translational Modification of Proteins in Insect Cells

Because baculoviruses infect invertebrate cells, it is possible that the processing of proteins produced by them is different from the processing of proteins produced by vertebrate cells. Although this seems to be the case for some posttranslational modifications, it is not the case for others. For example, two of the three posttranslational modifications of the tyrosine protein kinase, pp60$^{c-src}$, that occur in higher eukaryotic cells (myristylation and phosphorylation of serine 17) also take place in insect cells. However, another modification of pp60$^{c-src}$ observed in vertebrate cells, phosphorylation of tyrosine 527, is almost undetectable in insect cells (Piwnica-Worms et al., 1990, "Regulation of pp60$^{c-src}$ and its Association with Polyoma Virus Middle T Antigen in Insect Cells", *J. Virol*, 64:61-68.

In addition to myristylation, palmitylation has been shown to take place in insect cells. However, it has not been determined whether all or merely a subfraction of the total recombinant protein contains these modifications. Cleavage of signal sequences, removal of hormonal prosequences, and polyprotein cleavages have also been reported, although cleavage varies in its efficiency. Internal proteolytic cleavages at arginine- or lysine-rich sequences have been reported to be highly inefficient, and alpha-amidation, although it does not occur in cell culture, has been reported in larvae and pupae (Hellers et al, 1991, "Expression and Post-Translation Processing of Preprocecropin-A Using a Vaculovirus Vector", *Eur. J. Biochem*, 199:435-439). In most of these cases a cell- or species-specific protease may be necessary for cleavage. Protein targeting seems conserved between insect and vertebrate cells. Thus, proteins can be secreted and localized faithfully to either the nucleus, cytoplasm, or plasma membrane. Although much remains to be learned about the nature of protein glycosylation in insect cells, proteins that are N-glycosylated in vertebrate cells will also generally be glycosylated in insect cells. However, with few exceptions the N-linked oligosaccharides in insect cell-derived glycoproteins are only high-mannose type and are not processed to complex-type oligosaccharides containing fucose, galactose, and sialic acid. O-linked glycosylations have been even less well characterized in Sf9 cells, but have been shown to occur. For further information on protein processing in insect cells, see Jarvis and Summers, 1990, "Baculovirus Expression Vectors. In Recombinant DNA Vaccines: Rationale and Strategies" (R. E. Isaacson, ed.) pp. 265-291. Marcel Deckker, New York; and O'Reilly et al.

Steps for Overproducing Proteins Using the Baculovirus Expression System

A brief overview of overproduction of recombinant PGF proteins using the baculovirus expression system is presented below.

First clone the gene of interest into the appropriate baculovirus expression vector and prepare or buy linearized wild-type baculovirus DNA. Alternatively, purify circular wild-type baculovirus DNA.

Next cotransfect wild-type baculovirus DNA with the recombinant baculovirus plasmid into Sf9 cells.

Then collect the medium supernatant, which contains both wild-type and recombinant virus, and plaque the virus mixture on Sf9 cells to separate wild-type virus from recombinant virus.

Inspect the plaques to identify potential recombinants.

Then determine whether the potential recombinant viruses express the protein of interest.

Then plaque-purify the positive recombinants until free from any wild-type contaminants.

Reagents, Solutions, and Equipment for the Baculovirus Expression System

Commonly used reagents and solutions are summarized below.

1. Spodoptera frugiperda clone 9 (Sf9) cells from the American Type Culture Collection (#CRL 1711), Pharmingen (#21300C), or Invitrogen (#B825-01); Sf21 cells from Clontech (#K1601-E) or Invitrogen (#B821-01). These cells are derived from fall armyworm ovaries. Sf9 is a clonal line derived from Sf21.

2. Graces insect cell culture medium, supplemented with lactalbumin hydrolysate and yeastolate and unsupplemented, 1× and 2× strength in powdered or liquid form, from GIBCO/BRL. For instructions on media preparation from individual components, see O'reilly et al, 1992.

3. Serum-free insect cell culture medium (Sf-900 II from GIBCO/BRL or Ex-Cell 401 from JRH Biosciences).

4. Incubator at 27=/−1C; $CO_2$ is not required. The Biological Oxygen Demand (B.O.D.) low-temperature incubator (VWR Scientific) or the larger Isotemp (Fisher) are good examples.

5. Magnetic spinner flasks (Bellco; available in a variety of sizes).

6. Stir plate for multiple spinners (Bellco).

7. Fetal bovine serum (FBS) is available from many vendors. Obtain and test different lots of serum from a number of suppliers. The lot that promotes the best growth rate and cell viability should be purchased in bulk.

8. Seakem ME agarose (FMC Bioproducts).

9. 60-mm tissue culture plates (Falcon or Corning).

10. Antibiotics (optional)-gentamicin and amphotericin B (Fungizone from Flow Laboratories).

11. Microscope, either an inverted light microscope or a dissecting microscope.

Commercial kits are also available from Invitrogen, Pharmingen, and Clontech.

Although a preferred embodiment of the invention has been described with some particularity, many modifications and variations are possible in the preferred embodiment without deviating from the invention. Therefore, it is to be understood that, within the scope of the appended claims, the invention may be practiced other than as specifically described.

---

What is claimed is:

1. An isolated DNA which encodes plerocercoid growth factor having the amino acid sequence of SEQ ID NO:2.

2. A vector which comprises the DNA of claim 1.

3. A procaryotic or eucaryotic host cell transformed or transfected with an isolated DNA according to SEQ ID NO:1 in a manner allowing the host cell to express plerocercoid growth factor.

4. A vector according to claim 4 wherein said vector is a plasmid or viral vector comprising the DNA of claim 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 651 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..651

( x i ) SEQUENCE DESCRIPTION: SEQ ID NO:1:

```
CTT  CCC  GAC  AGT  GTT  AAT  TGG  CAC  GAG  AAG  GGT  GCT  GTT  ACA  TCG  GTC    48
Leu  Pro  Asp  Ser  Val  Asn  Trp  His  Glu  Lys  Gly  Ala  Val  Thr  Ser  Val
 1              5                        10                       15

AAA  AAT  CAG  GGT  CAG  TGC  GGA  TCC  TGT  TGG  TCT  TTC  TCC  GCA  AAC  GGT    96
Lys  Asn  Gln  Gly  Gln  Cys  Gly  Ser  Cys  Trp  Ser  Phe  Ser  Ala  Asn  Gly
             20                       25                       30

GCC  ATT  GAG  GGC  GCA  ATT  CAG  ATA  AAG  ATG  GGG  ATA  CTG  CGC  AGC  CTC   144
Ala  Ile  Glu  Gly  Ala  Ile  Gln  Ile  Lys  Met  Gly  Ile  Leu  Arg  Ser  Leu
         35                       40                       45

TCA  GAA  CAA  CAG  TTG  GTT  GAC  TGC  AGT  TGG  GAG  TAT  GGA  AAC  CAA  GGC   192
Ser  Glu  Gln  Gln  Leu  Val  Asp  Cys  Ser  Trp  Glu  Tyr  Gly  Asn  Gln  Gly
     50                       55                       60

TGC  AAT  GGA  GGG  TTT  ATG  TCG  CTG  GCT  TTT  CAA  TAC  GCT  CAA  AGG  TAC   240
Cys  Asn  Gly  Gly  Phe  Met  Ser  Leu  Ala  Phe  Gln  Tyr  Ala  Gln  Arg  Tyr
 65                       70                       75                       80

GGC  GTA  GAA  GCT  GAA  GTT  GAC  TAC  AGA  TAT  ACT  GCA  AAG  GAC  GGG  TTT   288
Gly  Val  Glu  Ala  Glu  Val  Asp  Tyr  Arg  Tyr  Thr  Ala  Lys  Asp  Gly  Phe
                         85                       90                       95

TGT  AGA  TAT  CAA  CAG  GAC  ATG  GTT  GTT  GCC  AAT  GTT  ACT  GGA  TAT  GCA   336
Cys  Arg  Tyr  Gln  Gln  Asp  Met  Val  Val  Ala  Asn  Val  Thr  Gly  Tyr  Ala
                 100                      105                      110
```

```
GAG CTA CCA CAG GGC GAT GAA GCA AGC CTC CAG AGA GCT GTT GCA GTC    384
Glu Leu Pro Gln Gly Asp Glu Ala Ser Leu Gln Arg Ala Val Ala Val
        115                 120                 125

ATA GGG CCC ATA TCT GTT GGA ATC GAT GCA AAC GAT CCC GGA TTT ATG    432
Ile Gly Pro Ile Ser Val Gly Ile Asp Ala Asn Asp Pro Gly Phe Met
    130                 135                 140

TCT TAC AGC CAC GGT GTG TTT GTT AGC AAA ACA TGC TCC CCA GAT GAC    480
Ser Tyr Ser His Gly Val Phe Val Ser Lys Thr Cys Ser Pro Asp Asp
145                 150                 155                 160

ATT AAT CAC GGC GTT CTG GTC ATC GGT TAT GGC ACG GAA AAT GAC GAG    528
Ile Asn His Gly Val Leu Val Ile Gly Tyr Gly Thr Glu Asn Asp Glu
                165                 170                 175

CCT TAC TGG CTG GTA AAG AAC AGC TGG GGG CGC TCC TGG GGT GAA CAG    576
Pro Tyr Trp Leu Val Lys Asn Ser Trp Gly Arg Ser Trp Gly Glu Gln
            180                 185                 190

GGA TAC GTC AAA ATG GCC CGC AAC AAA AAC AAC ATG TGT GGA ATT GCC    624
Gly Tyr Val Lys Met Ala Arg Asn Lys Asn Asn Met Cys Gly Ile Ala
        195                 200                 205

AGC GTG GCA TCT TAT CCA ACC GTG TAA                                651
Ser Val Ala Ser Tyr Pro Thr Val
    210                 215
```

( 2 ) INFORMATION FOR SEQ ID NO:2:

( i ) SEQUENCE CHARACTERISTICS:
        ( A ) LENGTH: 216 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Leu Pro Asp Ser Val Asn Trp His Glu Lys Gly Ala Val Thr Ser Val
 1               5                  10                  15

Lys Asn Gln Gly Gln Cys Gly Ser Cys Trp Ser Phe Ser Ala Asn Gly
                20                  25                  30

Ala Ile Glu Gly Ala Ile Gln Ile Lys Met Gly Ile Leu Arg Ser Leu
            35                  40                  45

Ser Glu Gln Gln Leu Val Asp Cys Ser Trp Glu Tyr Gly Asn Gln Gly
        50                  55                  60

Cys Asn Gly Gly Phe Met Ser Leu Ala Phe Gln Tyr Ala Gln Arg Tyr
65                  70                  75                  80

Gly Val Glu Ala Glu Val Asp Tyr Arg Tyr Thr Ala Lys Asp Gly Phe
                85                  90                  95

Cys Arg Tyr Gln Gln Asp Met Val Val Ala Asn Val Thr Gly Tyr Ala
            100                 105                 110

Glu Leu Pro Gln Gly Asp Glu Ala Ser Leu Gln Arg Ala Val Ala Val
        115                 120                 125

Ile Gly Pro Ile Ser Val Gly Ile Asp Ala Asn Asp Pro Gly Phe Met
    130                 135                 140

Ser Tyr Ser His Gly Val Phe Val Ser Lys Thr Cys Ser Pro Asp Asp
145                 150                 155                 160

Ile Asn His Gly Val Leu Val Ile Gly Tyr Gly Thr Glu Asn Asp Glu
                165                 170                 175

Pro Tyr Trp Leu Val Lys Asn Ser Trp Gly Arg Ser Trp Gly Glu Gln
            180                 185                 190

Gly Tyr Val Lys Met Ala Arg Asn Lys Asn Asn Met Cys Gly Ile Ala
        195                 200                 205
```

| Ser | Val | Ala | Ser | Tyr | Pro | Thr | Val |
|-----|-----|-----|-----|-----|-----|-----|-----|
|     | 210 |     |     |     | 215 |     |     |